United States Patent [19]

Aune et al.

[11] Patent Number: 5,023,805
[45] Date of Patent: Jun. 11, 1991

[54] LOG SCANNER

[75] Inventors: Jan E. Aune; Peter K. L. So, both of Vancouver, Canada

[73] Assignee: MacMillan Bloedel Limited

[21] Appl. No.: 235,282

[22] Filed: Sep. 28, 1988

[51] Int. Cl.[5] ..................... G01N 23/06; G01N 23/18
[52] U.S. Cl. .................................... 364/507; 378/51; 378/58
[58] Field of Search .................. 364/468, 507, 413.14; 378/9, 51, 58

[56] References Cited

U.S. PATENT DOCUMENTS 4,095,107  6/1978  Genna et al. ..................... 378/19 X
4,283,629  8/1981  Habermehl et al. .................... 378/4

OTHER PUBLICATIONS

McMillin, C. W. et al., "ALPS (Automated Lumber Processing System)—a Potential New Automated Lumber Processing System (Utilizing Tomographic Scanners, Optical Defect Analyzers, Lasers and Computers", *Forest Products Journal*, vol. 34, No. 1, Jan. 1984, 13-20.

Funt, B. V. et al., "Detection of Internal Log Defects by Automatic Interpretation of Computer Tomography Images", *Forest Products Journal*, vol. 37, No. 1, Jan. 1987, 56-62.

McMillin, C. W., "Automation and Computer Vision in the Rough Mill", FPRS Proceedings No. 47345, 1986, 117-124.

Conners, R. W. et al., "Identifying and Locating Surface Defects in Wood: Part of an Automated Lumber Processing System", *IEEE Trans. Pattern Anal. & Machine Intelligence*, 1982 Workshop on Industrial Applications of Machines Vision, Research Triangle Park, N.C., May 3-5, 1982, vol. PAMI-5, No. 6, Nov. 1983, 573-83.

Conners, R. W. et al., "A Prototype Software System for Locating and Identifying Surface Defects in Wood", *Seventh Annual Conference on Pattern Recognition*, Montreal, Quebec, Jul. 30-Aug. 2, 1984, IEE Comput. Soc. Press, vol. 1, 1984, 416-419.

Taylor, F. W. et al., "Locating Knots by Industrial Tomography-A Feasibility Study (Lumber Processing (List continued on next page.)

*Primary Examiner*—Clark A. Jablon

[57] ABSTRACT

A method of analyzing a body (log) containing elements (e.g. knots) having different densities than the remainder of the body by passing electromagnetic energy from at least one source for substantially symmetrical bodies (pruned logs) or at least two sources through the body and sensing the amount of energy passing through the body from each source by sensors mounted opposite each source. Each sensor is formed by an array of discrete detectors positioned in side by side relationship opposite their respective sources. The amount of radiation passing through the body is detected as the body passes between the source(s) and its (their) respective detector(s) and a longitudinal plan is generated based on the radiation detected from each of the sensors over at least a preselected length of the body. For non-symmetrical bodies the longitudinal plans are then analyzed to identify the same element in each of the plans and then the body is reconstructed in a plurality of cross sections representing discrete lengths of the body shorter than the selected length with the detected elements positioned in the cross section.

A longitudinal axis of the body is selected based on the shape of the body and the plurality of the cross sections are collapsed along lines parallel to the selected longitudinal axis to provide an accumulation of the overlying elements along the axis in a single cross section representative of the length of body being collapsed. This system provides a means for a real time analysis of a body such as a log to determine the location of defects and generate a rotation decision for rotating the log for presentation to the headrig to permit the optimization of a sawing solution for the log. The system may also be used to determine a bucking solution to select the length of the log for which the sawing solution is determined.

36 Claims, 9 Drawing Sheets

LOG SCANNER

FIELD OF THE INVENTION

The present invention relates to a system for scanning density within a body. More particularly the present invention relates to a system for determining internal defects in logs, locating the defects and determining a sawing solution based on the detected defects.

BACKGROUND OF THE PRESENT INVENTION

The disclosure will deal with logs but some of the technology described will have another application. The term defects is intended to include one or more of stones or nails or other intrusions in the tree and natural defects such as knots or rot or very low density volumes or voids.

It has long been a desire of the forest products industry to provide a system for internally examining the log to find its defects and then, based on defects and their location, automatically in "real time" provide a sawing solution to permit maximization of the wood recovery or lumber recovery from the log. By "real time" it is meant at a rate that keeps pace with the normal speed of operation of the sawmill particularly the headrig of the mill.

In the Fourth Nondestructive Testing of Wood Symposium in August 1978 in a paper entitled "Scanning of and Computing Methods for Measuring Knots and Other Defects in Lumber and Veneer" by Torbjorm Schmidt there was a brief description of the application of tomography to investigate defects in a log. In that description the exposure time for tomography was 37 seconds and the computer took two minutes to provide the resulting picture illustrating a cross section through one section of the log. It will be apparent that, while it was evident one could determine the internal structure of a log using tomography in 1978, it was simply impossible to do this in a time frame that was useful for control in a sawmill. This is particularly true when one considers that only a single cross sectional image was obtained in a two and half minute time frame.

In Wood Science (Vol 14, No. 3, p 97–104, January 1982) an article entitled "Application of Automatic Image Analysis to Wood Science" by Charles W. McMillan discusses automatic image analysis and describes scanning technology for primary log breakdown and for cutting clear furniture parts from defective boards. The use of computerized axial tomography "CAT-SCAN" to nondestructively locate defects in the log interiors is described.

The majority of the McMillan paper is directed toward image analysis of photographic images and is simply an indication of what might be accomplished. However none of the operations are done in "real time". These teachings are not useful for a commercial log scanner to determine a sawing solution in "real time".

In the McMillan article the concept of using a CAT-SCAN to determine the interior of a log is discussed as well the use of a plurality of such scans to define the x-y coordinates for a knot in each such cross sectional scan. McMillan suggests that the information from the cross sectional scans then be used in a computer to determine the log positions needed to maximize grade or value yield but provides no teaching on how this might be done.

In Forest Research Bulletin No. 8 (Feb. 19, 1982) there is a paper entitled "Computed Tomographic Scanning for the Detection of Defects within Logs" by Benson-Cooper et al. that also suggests that a sawing solution based upon CATSCAN information might be derived, but does not provide any teaching as to how one might obtain this objective.

BRIEF DESCRIPTION OF THE PRESENT INVENTION

It is an object of the present invention to provide a system for scanning and determining the locations and size of elements within the body.

It is also an object of the present invention to provide a log scanning system operable in real time to determine a sawing solution for a log based on the location of internal defects.

It is another object of the present invention to provide a system for separating a signal representative of elements of a selected density in an irregular shaped body of a different density wherein the generated signal incorporates a component representative of the shape of the body and a further component representative of the elements by determining that portion of the signal generated by the body and subtracting from the overall signal to provide a signal representative of the elements.

It is a further object of the present invention to provide a simplified system for identifying objects and their location within a body based on determining the axial ends of said elements in at least two projected plan views of the body determining the approximate size of the elements in each said plan and selecting as the same element those elements having substantially the same size and their end points located in said plan to use in the same pair of axially spaced planes said planes being substantially perpendicular to the longitudinal axis of said plans.

Broadly, the present invention relates to a method of identifying elements or defects of different densities in an image generated by projecting electromagnetic energy from a source through a non-uniform body traversing said source and developing an image representative of the attenuation of the electromagnetic energy in localized areas through the body by detecting the amount of electromagnetic energy passing through the body in such localized areas thereby to generate a signal varying in accordance with the density of the material of the body and of the elements obstructing passage of the electromagnetic energy through the body as said body traverses said scanner comprising developing a body geometry related signal indicative of the geometry of the body being sensed by eliminating major fluctuations in signal amplitude and subtracting said geometry related signal from said signal to provide a resultant signal and analyzing said resultant signal for areas of significant differences in signal strength.

A method of generating an image comprising passing electromagnetic energy from a source through a body containing elements of different density than the average density of the body, a sensor having a plurality of discrete detectors arranged in side by side relationship and adapted to receive electromagnetic energy from said source passing through said body, each said discrete detector detecting the amount of energy passing from said source through said body to said detector thereby to generate an image signal based on the degree of attenuation of electromagnetic energy received by each of the detectors, said body being of non-uniform thickness measured in the direction of electromagnetic energy propagation, eliminating a portion of said signal representative of said body by smoothing the signal from each detector to produce a body signal substantially free of major changes in amplitude and subtracting such body signal from said image signal for each detector to provide signals representative of said elements contained within said body.

Preferably there will be three such sensors (more may be used but 3 have been found to be adequate) and sources arranged at spaced locations around the body and each adapted to generate an image signal and wherein said body is moved relative to said sources to provide continuous plan image signals extending axially of said body in the direction of movement of said body relative to said sources, processing of said plan image signals to identify signal areas representing elements, analyzing each of said longitudinal plan to identify signals representative of the same element in each of the plans and reconstructing a cross section of said body with said element positioned in said body by a triangulation method.

One mode of identifying the same element in the various plans comprises finding elements in all plan image signals having their end points located in the same pair of spaced planes perpendicular to the direction of travel of said body past said sensors, determining the approximate size of each said element for each said plan, selecting as representing the same element those elements having their end points in each plan in substantially the same said pair of planes and determined as being essentially the same size.

A mode of identifying the size of an element comprises identifying a longitudinal axis for the element signal, determining the maximum width of said element signal perpendicular to said longitudinal axis, determining the position of the end points of said longitudinal axis, defining a pair of coinciding with said longitudinal axis and with their major diameter ends abutting and their pointed ends coinciding with the end points of said longitudinal axis, said major diameters being equal and equal to said maximum width, the combined volume of said pair of cones representing the volume occupied by said element.

In order to eliminate body geometry the basic axial density signal from each detector is filtered to suppress the high frequency information representing defects using successive convolutions applied to each channel (signal line extending perpendicular to the longitudinal axis) to provide a body geometry signal and subtracting the body geometry signal from the basic signal to provide a defect signal.

Broadly, the present invention also relates to a system for analyzing bodies (logs) to provide a basis for a sawing solution comprising conveyor means for transporting a log substantially longitudinally, density scanner means having means for passing electromagnetic waves substantially perpendicular to the direction of travel of said log, said scanner means including at least two discrete sources of electromagnetic energy, said sources being angularly spaced around said conveyer means to pass electromagnetic energy from at least two different directions, 25 through said log as it is conveyed past said scanner means, sensor means for sensing the amount of said electromagnetic energy passing through said log from each of said sources, each of said sensor means being composed of a plurality of discrete detectors circumferentially positioned relative to said log in side by side relationship opposite their respective of said sources and each adapted to detect the amount of radiation it receives from its respective source to provide discrete values for the degree of attenuation of electromagnetic energy between each said discrete detector and its respective said source, each detected by said sensor means over the length of said body, means for defining areas depicting different densities representing defects in each said plan, means for identifying areas in each of said plans representing the same element in the body in each of said longitudinal plans and means for reconstructing spaced discrete cross sections through said body positioning said elements in said cross section each said cross section being representative of a preselected length of said body traversing said scanner.

Preferably a longitudinal axis is selected for a selected length of said log and said discrete cross sectional views are collapsed along said axis to provide a projected cross sectional view of a selected length of the log identifying the propensity of such elements in various areas of such projected cross section.

The propensity of elements in a given area may be determined by providing a selected value per unit length measured in such axial direction for each such element in each of said cross sections. Preferably the rate of change in the area (volume) as fewer knots are included is used as a means for determining an area or volume for a knot core.

Preferably a rotation decision is to rotate said log to a given angular position for presentation to a headrig will be based on the location of said elements and the propensity of such elements in areas of said projected cross section preferably on the major diameter of the projected cross section of the knot core.

The system of the present invention also preferably when desired will determine a bucking solution for the log being processed and the length of log for which a sawing solution is to be found will be selected based on the bucking solution.

BRIEF DESCRIPTION OF THE DRAWINGS

Further features, objects and advantages will be apparent from the following detailed description of the preferred embodiments of the present invention taken in conjunction with the accompanying drawings in which.

DESCRIPTION OF THE PREFERRED EMBODIMENTS

Figure 1:
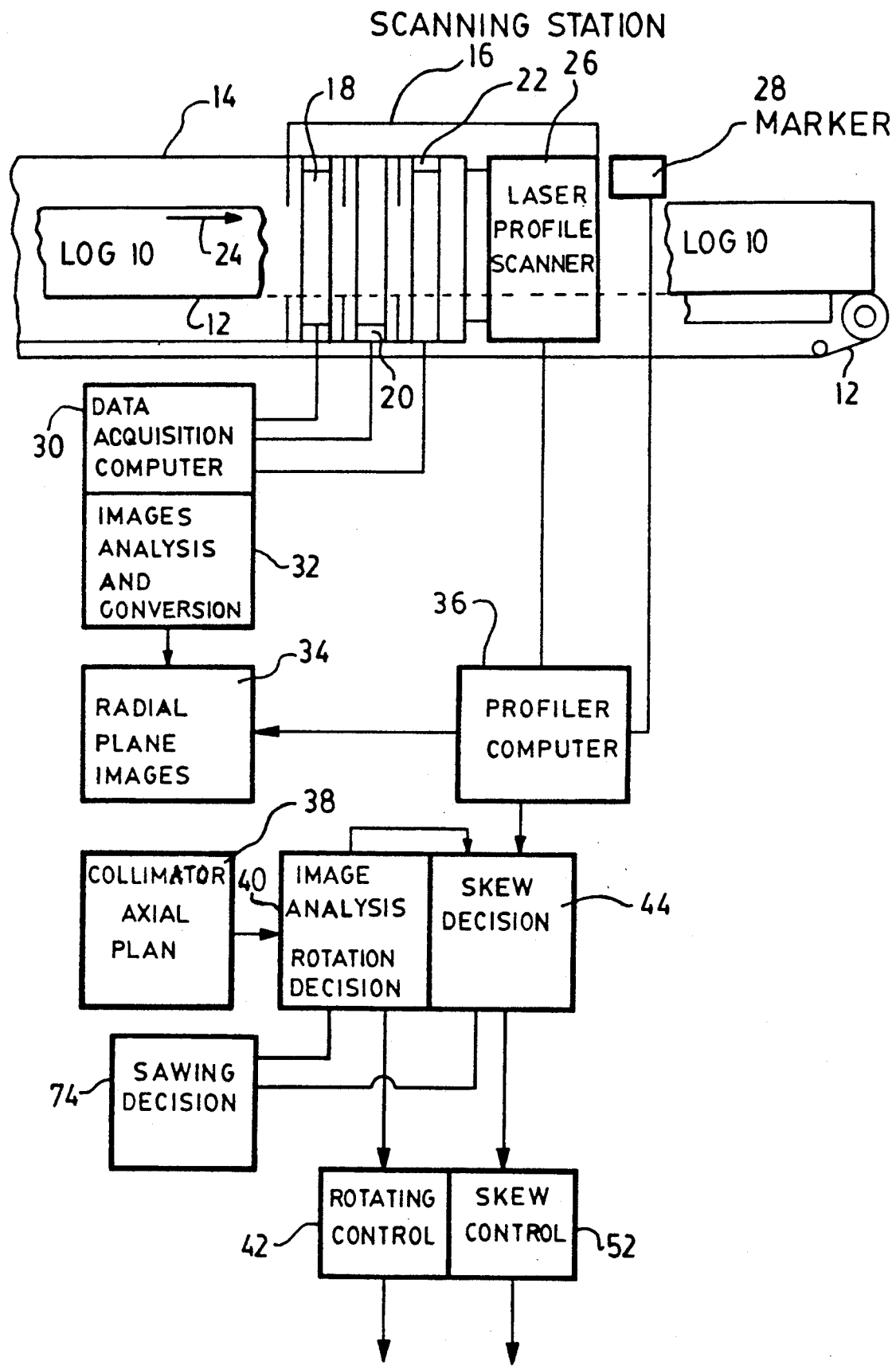
FIG. 1 is a schematic representation of scanner system incorporating the present invention.

As shown in FIG. 1 a log 10 is carried on a conveyor 12 through an inlet housing 14 which preferably is designed to prevent the escape of radiation. The log is carried on conveyors through a scanning station 16 which includes preferably at least three scanners 18, 20 and 22 (two may be used but are not recommended as proper resolution is difficult) each passing electromagnetic waves substantially in a plane perpendicular to the direction of travel of the conveyor 12 so that the waves pass through the log on paths in a plane substantially radial (perpendicular to the direction of log travel) to the log as the log is carried by the conveyor 12 in the direction of the arrow 24 through the station 16. Generally each of the scanners 18, 20 and 22 will pass electromagnetic energy, e.g. x-rays, through the log to determine the local density of the log, as will be described below.

Also included within the scanning station 16 is a laser profile scanner 26 which determines the outer dimensions of the log as it traverses the station 16 on a conveyor 12.

The laser profile scanner 26 may be used to mark the log 10 as it passes using a marker mechanism 28 which may take the form of a router, a paint spray or the like, tracing a line along the log preferably along the line defining the log periphery's maximum spacing from the face of the conveyor 12. This line may be subsequently used either in a bucking solution or as a datum for rotation of the log, as will be described below.

At least that portion of the conveyor 12 passing through the scanners 18, 20 and 22 preferably is a belt-type conveyor made of suitable material that does not interfere significantly with the operation of the scanners 18, 20 and 22. Some of the electromagnetic waves will be passed through the conveyor 12 to ensure the full cross section of the log is inspected.

Figure 2:
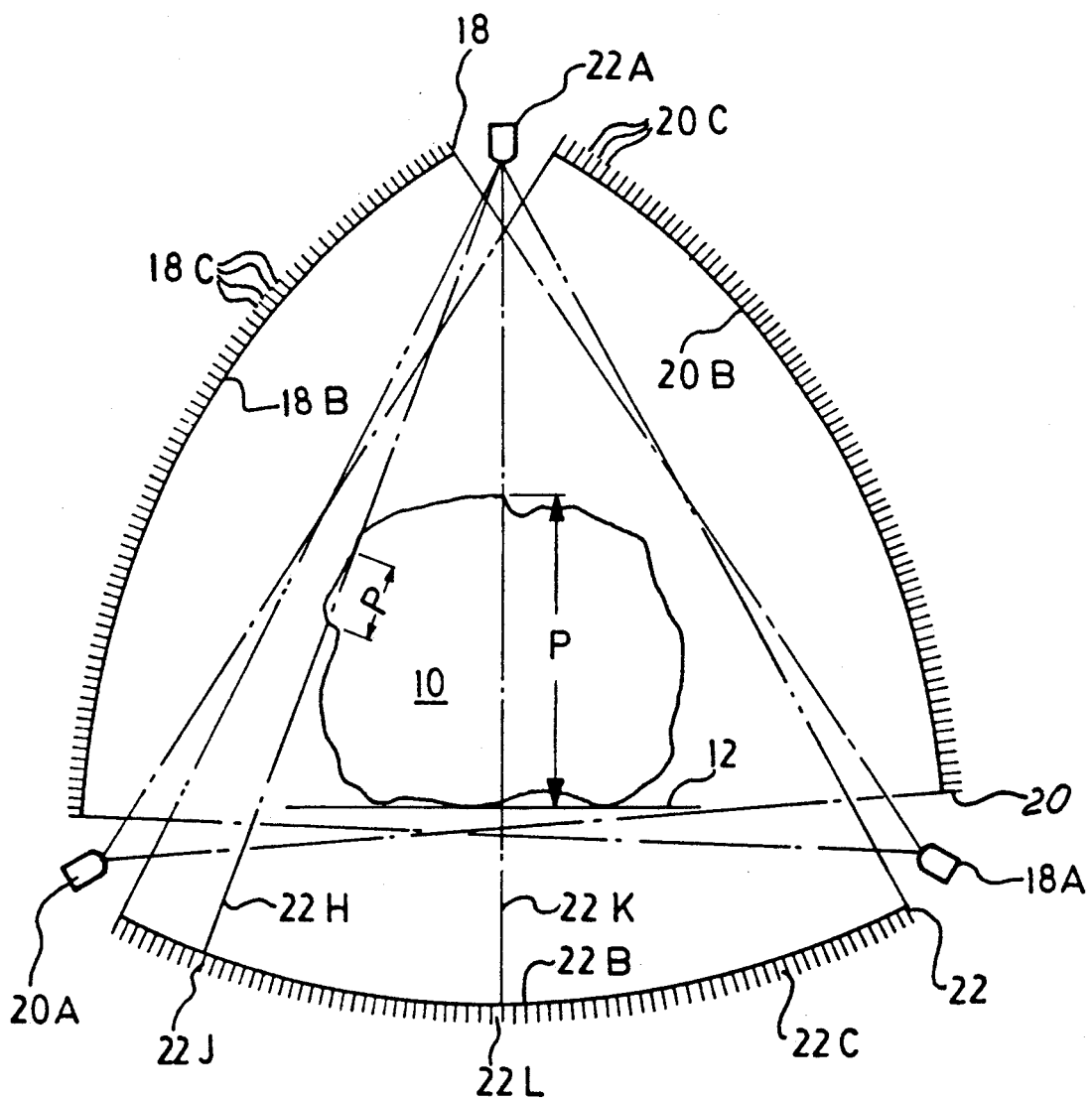
FIG. 2 is an end view illustrating a scanner having three angularly spaced radiation sources and corresponding sensors.

The scanners 18, 20 and 22 are spaced along the length of the conveyor 12 however, for convenience in FIG. 2 all have been shown in essentially the same plane.

The scanner 18 includes a radiation source 18A and a sensor or detector array 18B positioned directly opposite the source 18A. Sensor 18B is composed of a plurality of discrete detectors 18C which preferably are approximately one-quarter inch in length measured in the axial direction of travel of the conveyor 12 and a similar width in the circumferential direction along the curvature of the detector 18B which preferably will be essentially on an arc the center of which coincides with the source 18A.

The other scanners 20 and 22 include similar components each of which is indicated by the number of the scanner followed by the letter as described for scanner 18.

Figure 3:
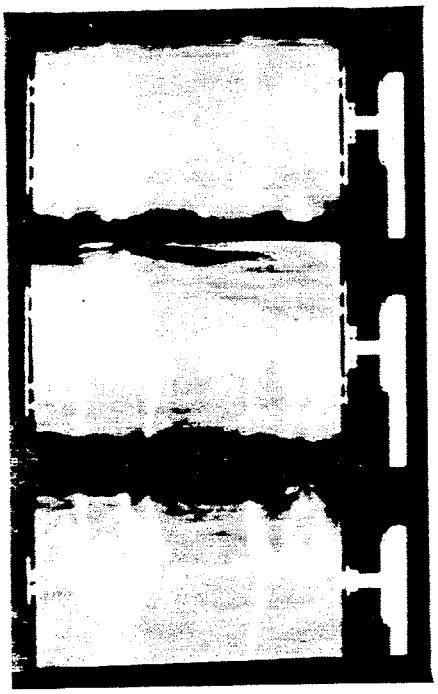
FIG. 3 illustrates typical axially extending density plans of lengths of the log as obtained one from each of the three sensors.

Each of the scanners 18, 20 and 22 is used to generate an axial extending density plan based on the attenuation of the electromagnetic energy by the log as the energy passes from the sources 18A, 20A and 22A to their respective sensors 18B, 20B and 22B. Such a set of three axially extending density plans or projections are illustrated in FIG. 3 for a selected length of one particular log (axially plans of the whole length of the log are generated as the log passes through the sensing station 16).

It will be noted that all of the projected plans are different, each being representative of density variations through the log at the different angles at which the sources project radiation through the log and as sensed by the detectors 18C, 20C and 22C as the log continually passes the scanners 18, 20 and 22. These longitudinally extending density plans are adjusted by calibration factors in the data acquisition computer section 30 (FIG. 1) and have been designated as plans 18D, 20D and 22D in FIG. 3 (the numeral corresponds with the sensor detecting the particular image). It will be apparent that each discrete axial length of one of the plans is matched (aligned on the same plane) with a corresponding discrete axial length in the other plans.

Figure 4:
FIG. 4 is a filtered image of the plans of FIG. 3 showing knots.
Figure 5:
FIG. 5 is a thresholded image derived from the plans of FIG. 4.

The images acquired by the computer section 30 are then analyzed, for example, in a further computer section 32 by filtering (FIG. 4) and thresholding the images (FIG. 5) based on the gray scale analysis, i.e. the images 18D, 20D and 22D vary in brightness depending on the local densities of the log which in turn indicates the degree of attenuation of the radiation passing through the log at each location.

Figure 6:
FIG. 6 illustrates three similar plan views after region growing depicting knots.

In FIG. 6 refined versions of the images 18D, 20D and 22D are shown as 18F, 20F and 22F respectively which clearly indicate the outline of the knots or high density areas in their respective density plans.

It will be apparent that since the log is of non-uniform cross section, for example may be substantially oval or circular in cross sectional shape, the length of the paths of travel of the electromagnetic energy rays through the log will be different in different areas of the log. Attention is again directed to FIG. 2. The ray 22H which is detected by the detector 22J passes through a thickness of the log 10 as indicated by the distance p whereas the ray 22K detected by the detector 22L passes through a thickness of log 10 indicated at P. It will be apparent that the attenuation of the ray 22H due to the body of the log perse is significantly less than the attenuation of the ray 22K simply because ray 22H passes through less wood than does the ray 22K and thus the signal produced by the detector 22J regardless of whether or not it traverses a defect in the log, will be significantly different than the signal generated by the ray 22K and will bias the scanning results accordingly. It is important that this portion of the signal as determined by body geometry be eliminated or rendered substantially insignificant so that the defects can be discerned.

To eliminate the body geometry portion of the signal as represented by the different thicknesses p and P the signal generated by each of the discrete detectors 22C for example the detector 22J and 22L are each processed individually along the length of the scan, i.e. in the direction parallel to the direction of movement of the log passed the source 22A. Each of these discrete detectors 22C represents a channel in the image generation system and each of these channels is processed independently in a manner to distinguish discrete elements such as knots or rot from the remainder of the body of the log. This can be accomplished by a variety of different techniques including, for example, edge detecting, image shifting and subtraction or multiplication and edge detection or subtraction.

A preferred system of identifying defects within a resultant scan of a selected axial length of the log is to process a signal from each channel by successively convoluting the signal with a set of one-dimensional low pass filters and then subtracting the convoluted signal from the original signal thereby leaving only the high frequency defect information. Preferably the width of the low pass filters will be increased by a significant margin on each successive pass for example, the filtering sequence could be first on two pixels, i.e. ½ filter, next in the sequence on 4 pixels, i.e. ¼ filter, on eight pixels, i.e. ⅛ filter and assuming five passes, 16 pixels and 32 pixels and the final convoluted signal subtracted from the original signal to provide a signal indicative of the defects detected by each discrete detector 22C such as detector 22J or 22L, i.e. by each channel.

Another approach for determining a defect signal from the signal contaminated with information relating to the body itself, is to determine defect edges using an edge detector applied along each channel and masking out each detected defect or high density area thus generating a defect mask image for that channel. This defect mask image is then subtracted from the original image or signal to provide a defect signal.

After the defect signal has been generated it is preferred to normalize same preferably to value of where all defects are either above or below a selected value, for example in a system with a range of 256 a value of ½ the range or 128 might be selected which will confine random noise to about this value. When processing logs, nails and rocks have been found to threshold above 140 on such a normalized signal and knots with rot are above about 130 while dry rot and voids are located below the 128 value at about 125. Binary images can then be produced for each of the defects by thresholding the normalized images at the appropriate level to produce such binary images and region growing the binary images into objects.

In the event the logs being processed or the bodies being processed are all substantially symmetrical about a longitudinal axis, for example as may well be the case for logs produced from properly pruned trees which confine their knot location in the pruned length to a substantially cylindrical axial portion of the tree and axially spaced swirls. In such a case sufficient information may be available from processing a single axial image and identifying the size and position of the knot core and swirls in the one image (the other images will be quite similar) and use this information in determining a sawing solution, i.e. only a single scanner such as scanner 18 may be necessary.

It will be apparent that in most normal logs, a single axial plan view will not be sufficient and while two views may be used to determine the location of knots or other defects and position them in a reconstructed cross section, the accuracy of such a system is not as good as that obtained by using three separate sources and three sensors to provide three axial plan images. Thus the remainder of this description will relate primarily to the use of three sources and three sensors and detecting and positioning defects within a body (log) based on three circumferentially spaced sensors as shown in FIG. 3 generating three axial plan images.

The various defects or high density areas illustrated in the three axial plans 18D, 20F and 22D are analyzed to determine corresponding areas for the same defect or knot in each of the plans 18F, 20F and 22F.

Figure 7:
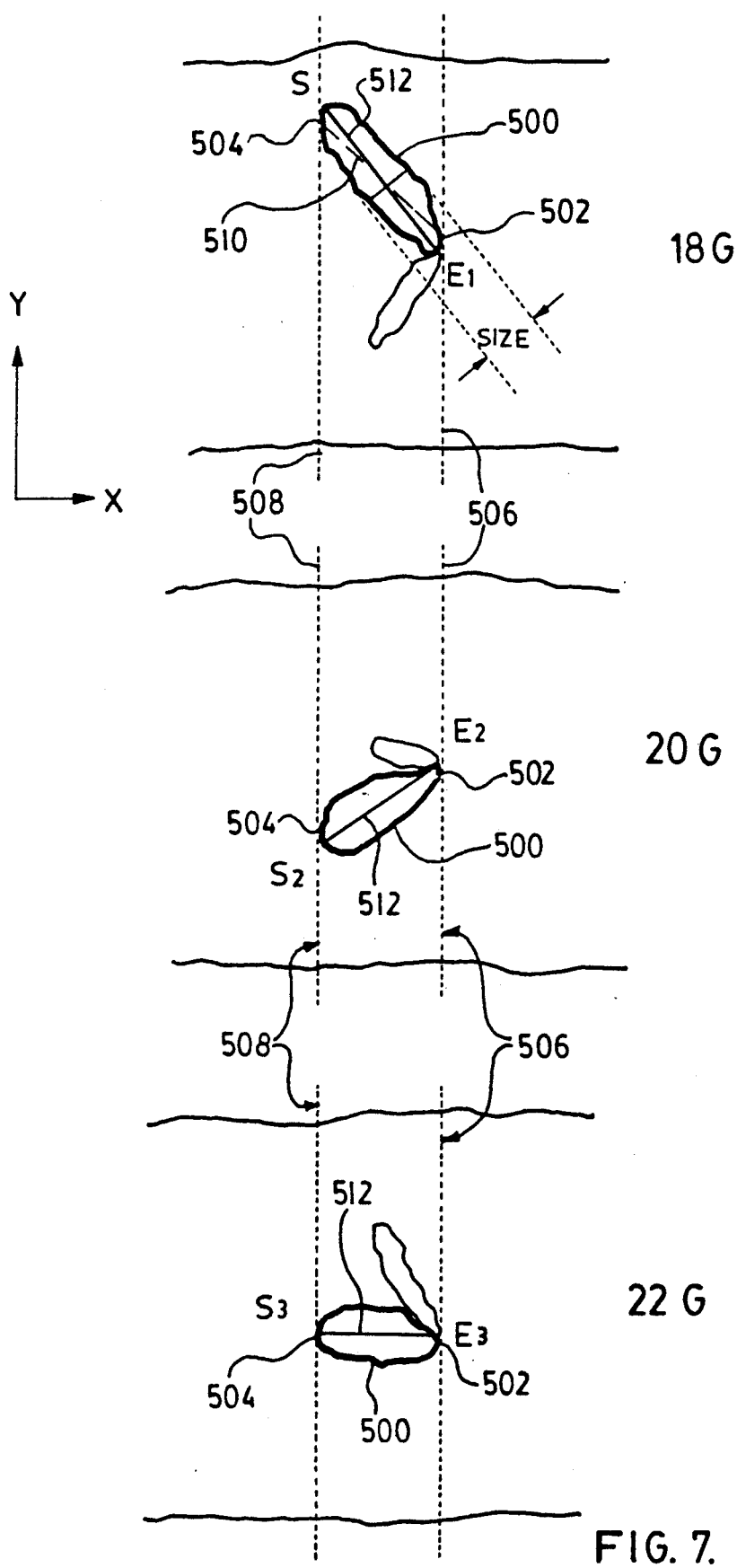
FIG. 7 illustrates a common section of the plan views of FIG. 6 showing the same element in each plan.

To determine whether areas in the various plans are areas representing the same element, the plans 18F, 20F and 22F are analyzed. To illustrate the process attention is directed to FIG. 7 wherein a selected longitudinal segment at the same axial position along the log for each of the plans 18F, 20F and 22F are illustrated by plan segments 18F, 20G and 22G. These plans 18G, 20G and 22G show an element or defect 500 which has its end points 502 and 504 in corresponding or the same pair of spaced radial planes 506 and 508 respectively in the various plan segments 18G, 20G and 22G.

These end points 502 and 504 may be used to define a selected longitudinal axis indicated by the dash lines 510 in view 18G. Similar selected axis can be determined for each of the views 20G and 22G for the element 500. However, it is preferred to determine an axis for the element 500 in all of the views using the well-known technique of a robust estimation to determine the axis as indicated at 512 where the defect 500 in each of the views 18G, 20G and 22G.

In each of the views 18G, 20G and 22G the maximum width perpendicular to the selected axis 512 is determined to provide an indication of the size of the defect 500. By comparison of the relative size, location and major axis of the elements in the various view elements having their axial end points 502 and 504 (axial extremities measured substantially axially of the view which in turn is axial of the log) in substantially the same spaced transverse planes 506 and 508 (perpendicular to the axis, i.e. radial planes relative to the view or the log and substantially corresponding in size will be accepted as being the same element).

Figure 8:
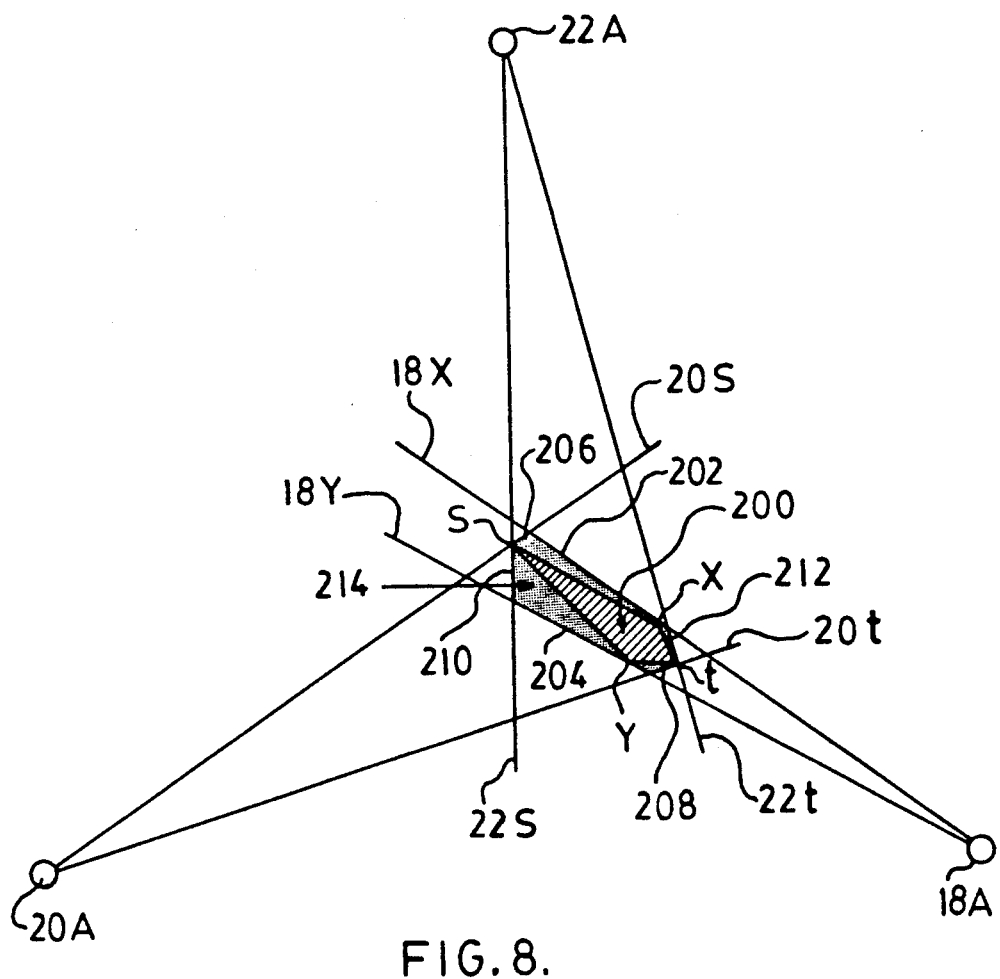
FIG. 8 illustrates a system for delineating a defect (knot) in a bounding polygon the size of which is determined by the detected extremities of the defects.
Figure 9:
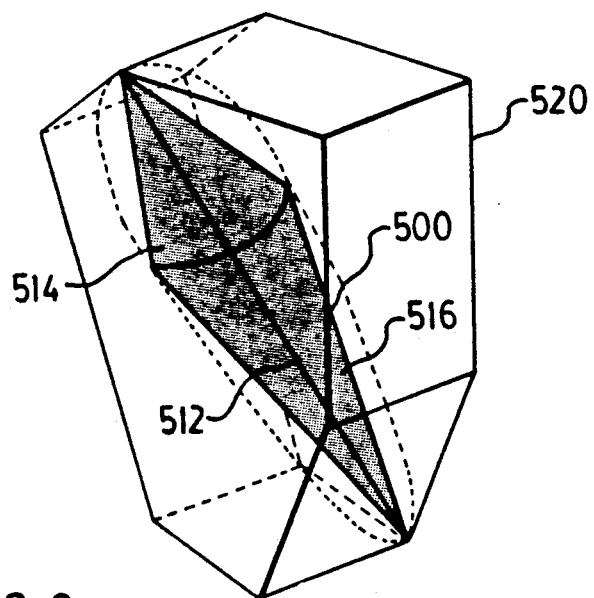
FIG. 9 illustrates a bounding polygon in 3 dimensions as well as a second method of estimating an element size that particularly suited to knots.

After the corresponding knots have been detected the extremities of these defects or knots based on the angular projection from each of the sources 18A, 20A and 22A for each of the respective images is used to define a bounding polygon for the defect (see FIG. 8).

In FIG. 8 a knot 200 has been depicted by cross-hatching and its extremities are detected for example, the x-ray source 18A determines two extremities as indicated by the lines 18X and 18Y which define the extremities x and y of the knot 200 as detected by detectors 18C. Similarly the extremities s and t are determined by the detectors 20C as depicted by the lines 20s and 20t and similarly the extremities s and t are detected by the detectors 22C based on the lines 22s and 22t. It will be seen that a combination of these lines 18X, 18Y, 20s, 20t and 22s, 22t define the side wall 202, 204, 206, 208, 210 and 212 respectively of a bounding polygon 214 for the knot 200. In many cases the inner extremity (adjacent the heart of the log) which, in the illustrated arrangement is say boundary s may be confused by the overlap of adjacent, but different knots. In this case, the defined centre line of the log will be used as the inner extremity equivalent to extremity s.

After the knots have been identified and their bounding polygons determined for each of a plurality of discrete axially spaced radial sections, these sections are converted to a binary system wherein each bounding polygon 214 in each discrete radial image is given a particular value, i.e. say a signal value of (1) and defect free wood is given a second signal value say (0) to provide a binary image for each cross section.

A gray scale value is then applied to each bounding polygon.

Gray scale values will depend in part on the length of the defect measured axially of the log.

Generally the gray scale value applied to any given cross sectional image will depend on the axial length of the log represented by a given cross sectional image and the total length of the log to be processed as will be described herein below. Thus, for example, the gray scale value for a defect might be determined by $$G = NP$$

where

G = grey scale value
N = the Number of discernable levels of gray scale, and $$P = \frac{\text{axial length of the discrete cross section}}{\text{axial log length being processed}}$$

Generally the axial length of a discrete cross section will represent about 4 inches measured in the direction of travel of the log as this length has been found to provide an adequate assessment. One foot has also been used and found to be satisfactory but it is preferred to use 4 inches as the short length permits better resolution. Similarly shorter axial lengths, i.e. less than 4 inches may be used for each discrete cross section. This will increase the number of cross sections that have to be accumulated as will be described herein below to determine the projected cross sectional image for the log, and will also improve the resolution if required.

Generally shorter than 2 inch axial length sections or slices are not warranted as the time for processing increases with each additional operation, while a slice length of 2 feet or even 1 foot reduces the resolution to the point where the time savings do not warrant the reduction in quality or resolution.

The log analysis may also be take into consideration the frequency of knot occurrences over the length of the log such that if there are a plurality of axially aligned knots with an intervening length between one pair of axially adjacent knots of say 8 feet this may be recognized and considered in making the sawing decision.

As the above operations are being carried out, the profile scanner 26 which will normally be any one of a number of commercially available laser scanners provides a signal to a profile computer 36. This computer is used to interpret the signal from the scanner 26 to select a longitudinal rotational axis for the log as indicated by the rotational axis x—x in FIGS. 15 and 16.

Various techniques may be used to find this hypothetical axis. One of the simpler ways is to determine the centers of the leading and trailing ends of that portion of the length of the log that is to be processed and to use as the hypothetical or longitudinal axis x—x the line interconnecting these centers.

Other more complicated techniques may be used to define the longitudinal rotational axis x—x, for example a least squares method based on the sensed profile of the log.

It will be apparent that as the length of log being processed changes so will the x—x rotational axis, i.e. the rotational axis will be in part dependent upon a bucking decision, if any, with respect to the log being scanned.

A bucking decision may be made in any suitable or conventional manner, for example, manually or by sensing the curvature of log using the profile scanner 26.

Figure 10:
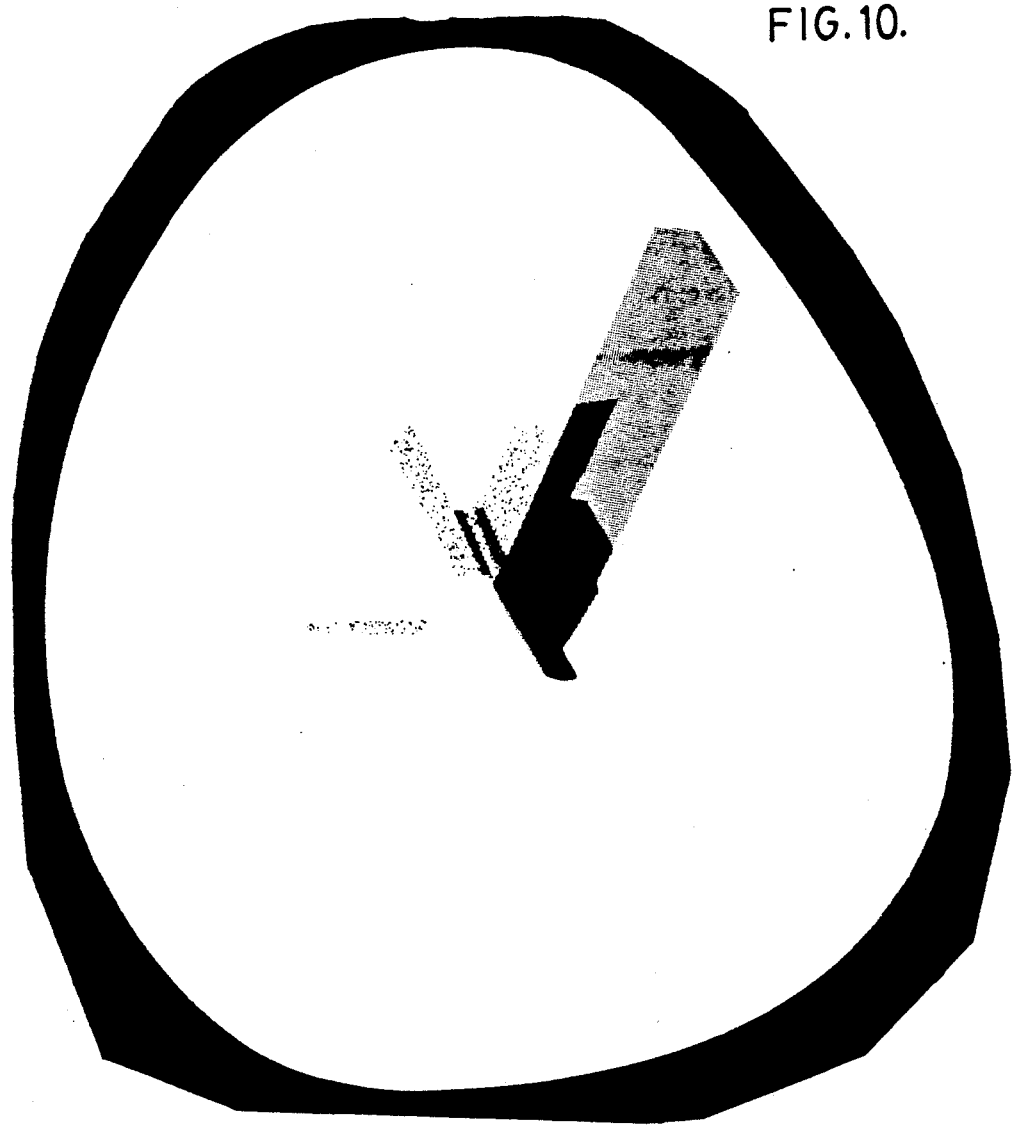
FIG. 10 illustrates an axially projected cross sectional image derived by axially projecting to superimpose bounding polygons of knots in a plurality of discrete axially spaced radial cross sectional images.

This longitudinal x—x rotational axis as determined above is used with the radial plane images generated by the computer 34 to axially project or collapse the radial plane images along lines parallel to the longitudinal x—x rotational axis to provide an accumulated cross sectional picture or map for a selected length of the log indicating the accumulation of defects in a given axial line. Such accumulated images are illustrated in FIG. 10.

The resulting accumulated radial cross section image or density map is thus composed by superimposing the reconstructed radial images which have been given a signal ratio based on the length of the log being processed such that the axial accumulation of axially overlapping knots results in a particular tone of the gray scale image in the accumulated cross sectional density map.

Suitable means for so accumulating the radial images and producing the accumulated radial density map is represented by the computer 38 (see FIG. 1).

The resultant accumulated radial image is then subjected to image analysis in the computer section 40 to determine the boundaries which delimit substantially clear wood from substantially knotty wood. The computer 40 analyzes the gray scale image for example in the image illustrated in FIGS. 10 or 11 to determine the knot location and propensity of knots in given locations and arrives at a rotation decision, i.e. the angle about rotational axis x—x that the log should be rotated for presentation to the saw.

Such an analysis of the accumulated radial image may be done in several different ways. For example, thresholding the accumulated radial image based on a selected degree of brightness (bearing in mind that each knot area had essentially the same brightness in each of the discrete cross sections that are accumulated) to determine clear and knotty areas and classify knotty areas with various degrees of knot propensity and assign values to the areas. Based on these analyses the quality of the wood that may be cut from any particular section can be determined.

The preferred system for finding the common knot core and examining the core includes boundary tracing thresholded areas after the threshold process and further reducing the boundary points between the thresholded areas and the adjacent areas by a co-linearity test utilizing the split merge algorithm that
1. sub-divides the boundary points,
2. processes the two segments,
   2.1 draws a line through the dividing end points of the segment,
   2.2 if the distance of the line to the furthest point of the given segment is greater that a pre-set allowed distance, the segment is split at the farthest point and the process in 2 above is repeated.
   2.3 if the distance is less than the pre-set allowed the segments are merged.

After the end points of the boundary are determined by the co-linearity test a convex hull algorithm such as the Jarvis algorithm "On the identification of the convex hull of a finite set of points in the plane" (Information Processing Letters, Vol. pages 18-21 (1973) is applied. This algorithm finds the lowest point in a data set and uses it as the first current base point, i.e. the first vertex of the hull. The next base point is selected such that it forms the smallest positive angle in relation to the then current base point and this next base point then becomes the current base point for the next vertex of the hull. This procedure is iterated until the next base point is the first base point at which time the complete boundary hull is formed.

Figure 11:
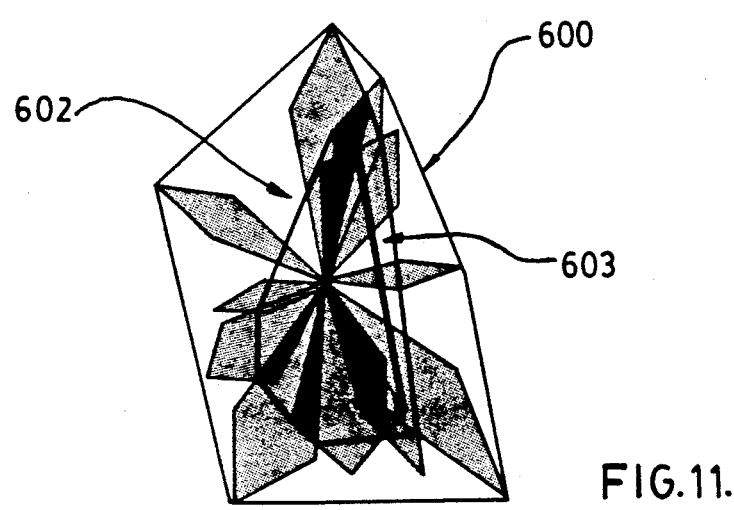
FIG. 11 illustrates different thresholding values for the projected cross sectional images.

FIG. 11 illustrates a series of bounding polygons applied to an image. In the series illustrated the bounding polygon 600 bounds that area that contains at least one defect and is based on a threshold value of a grey scale for one defect. Bounding polygon 602 has its periphery based on grey scale value for at most 2 defects. Bounding polygon 603 illustrates three defects, i.e. the more defects within a bounding polygon, the darker the images contained therein.

When the convex hulls are identified for each selected thresholding value, their areas are multiplied by the log length to determine volume of the bounded core and the ratio of this bound volume over an estimated log volume based on analysis of the log, may be plotted against its respective threshold value.

Figure 12:
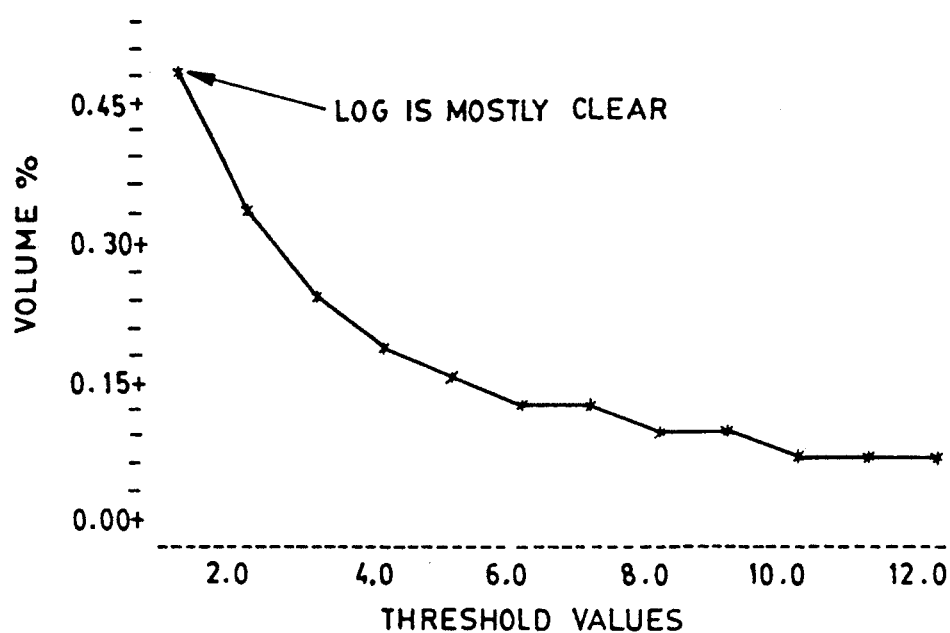
FIG. 12 is a plot of grey scale threshold values representing number of knots vs volume as a percentage of the whole body.

The number of thresholding values will vary but it is preferred to take a plurality of such threshold values, determine the volume of the bounded core, and provide a plot of such volume or percent of such volume relative to the total volume of the log against the threshold values as shown for example in FIG. 12. This information may then be used by converting same into rate of change, i.e. differentiating the curve of FIG. 12 to provide the rate of change of volume as the thresholding value is increased. In the illustration in FIG. 13, it can be seen that the rate of change is relatively high or what is defined as high value wood whereas common wood shows a rate of change versus threshold value that is relatively small. In the FIG. 13 the boundary between the knot or common core and the high value wood is indicated by the boundary level which, in this case, has a threshold value of 4.

Figure 13:
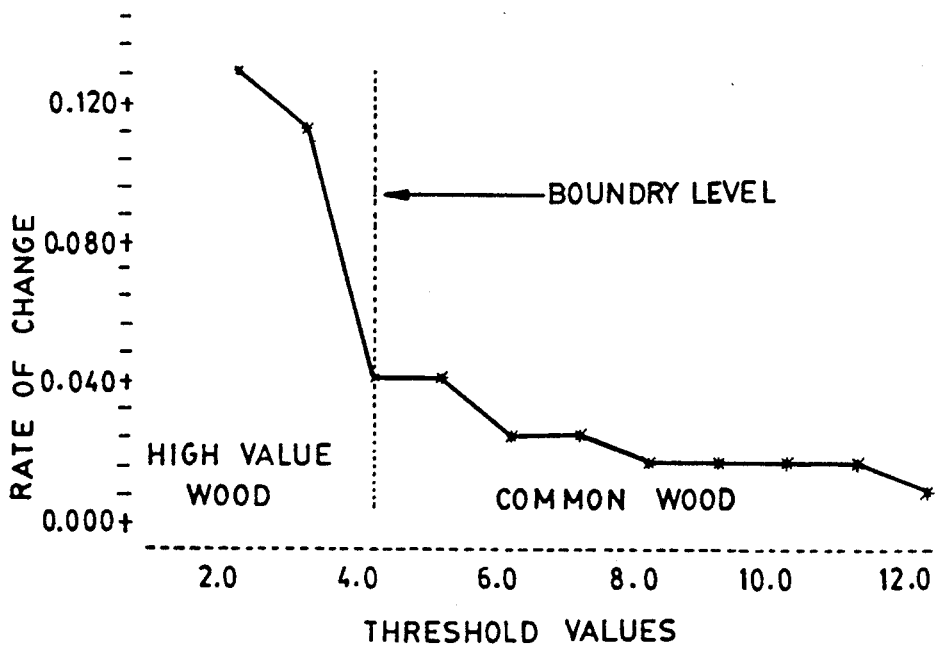
FIG. 13 is a plot of rate of change of volume vs. threshold values representing number of knots.
Figure 14:
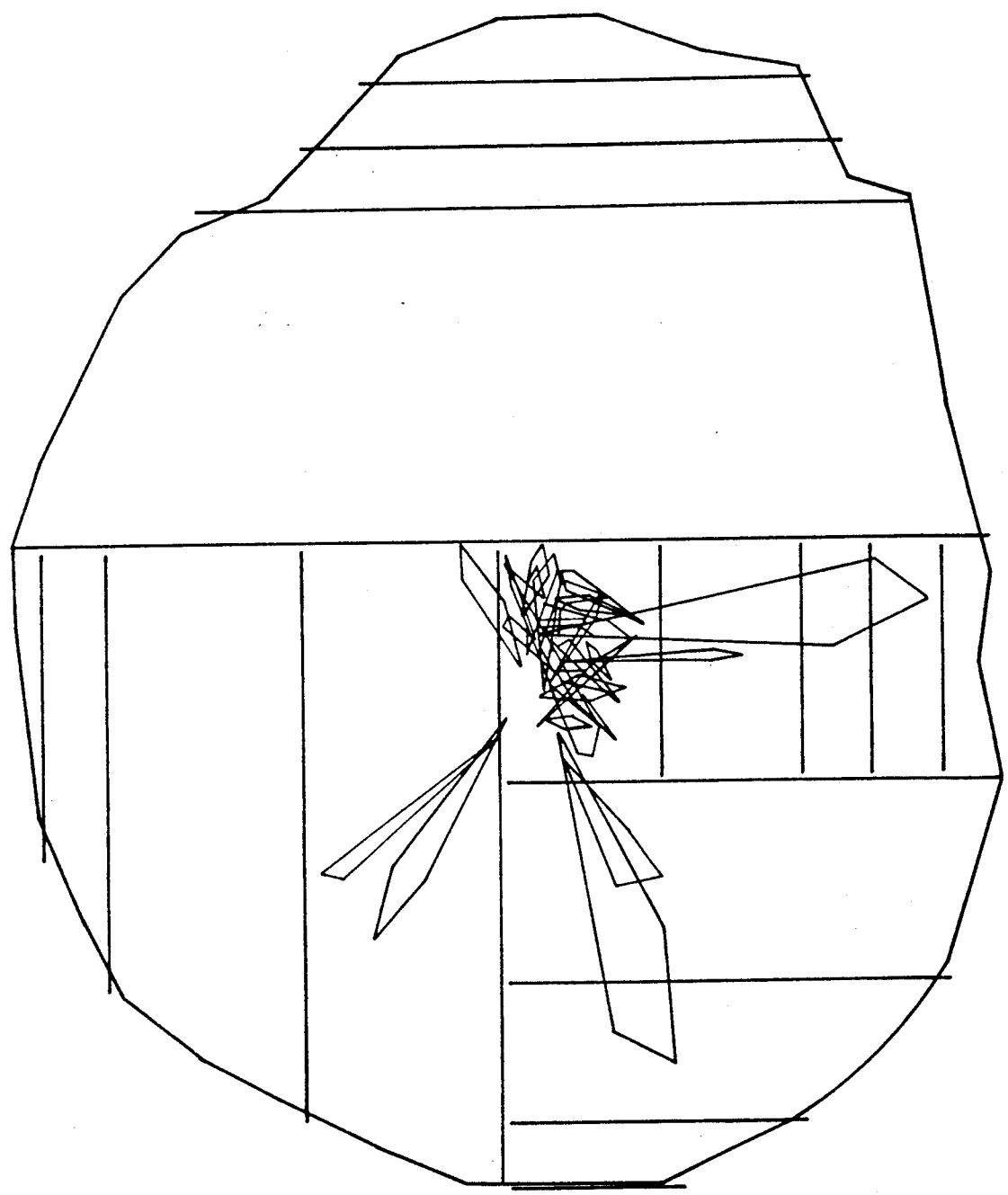
FIG. 14 shows a possible sawing solution based on analysis of the log.

Generally it has been found that clear or high value wood has a high rate of change of volume, shop wood has a lesser rate of change and common wood has a low rate of change. In the example of FIGS. 12 and 13 the common core has a rate of change of less than 0.01.

The above technique provides one way of defining the common knot core for a log. It is also possible to determine the knot core empirically based on a particular selection of threshold value and utilize that empirically selected threshold value for determining the common or knot core for example by forming a bounding polygon based on the selected threshold value. Such a system is less accurate than the thresholding system as described with respect to FIGS. 12 and 13, but does provide a simpler method.

Generally the rotational decision will be based on aligning one of the cutting planes substantially parallel to the longest diagonal of the knot accumulation or common core for example the longest diagonal for the bounding polygon for the knot core as defined above.

The other cutting plane will be substantially perpendicular to the longest diagonal and normally a rectangle will be determined that incorporates the common knot core and has one side parallel to the longest diagonal to redefine the knot core for the sawing solution.

The rotational decision based on such image analysis made by rotation decision computer 40 is fed to a rotational control schematically indicated at 42 and also to the profile computer 36.

Figure 15:
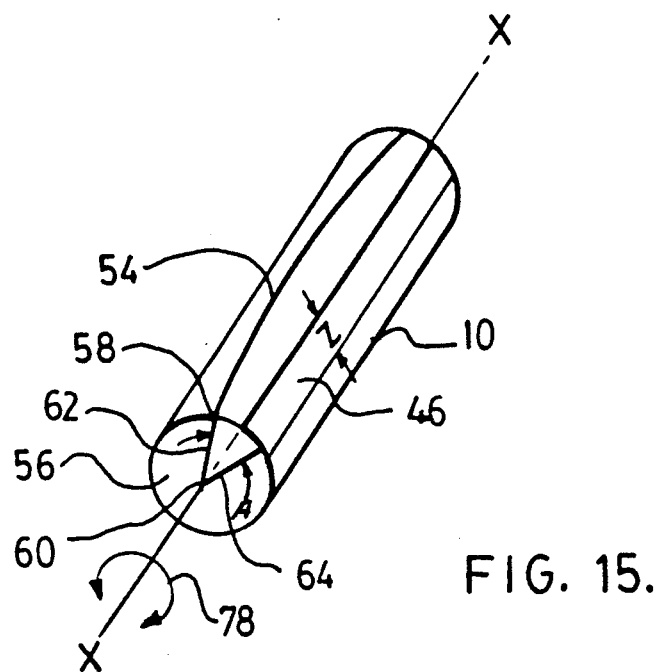
FIG. 15 is a schematic representation of a log depicting one manner in which the rotational angle for the log may be represented, illustrating a datum for angularly rotating the log and a minimum opening face.

To facilitate operation of the rotational control either manually or automatically, the location of the axial center line x—x (rotational axis) relative to one point on the periphery of the log at least one end of the log 10 must be known so that the angular rotation or displacement of the log 10 around the axis x—x as indicated by the angle A in FIG. 15 can be determined relative to a datum. In FIG. 15 the line described by marker 28 has been indicated at 54 and the junction of this line with the leading face 56 is indicated at 58. This junction is connected by a line 62 to the axis x—x in the selected center as indicated at 60 of the front face 56. The decision which is depicted by the line 64 extending from the center 60 to the outer periphery of log.

One of the opening faces or cuts is made substantially perpendicular to the line 64. If this first cut is to be parallel to this opening face the line 64 must be oriented by rotation of the log to be substantially perpendicular to that of the cut. This then defines the angular or rotational position of the log relative to the saw. Alternatively the first cut or opening face may be parallel to line 64 and the log will be rotated so that the plane of the saw is parallel to the line 64.

Figure 16:
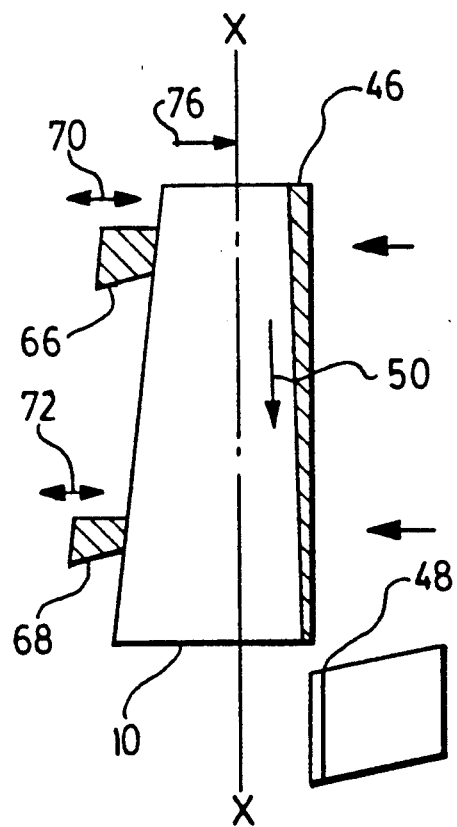
FIG. 16 is a schematic plan view illustrating skewing of the log for presentation to the saw.

Once the rotation decision is made the information from the profile computer and rotation decision are fed to the skew decision computer section 44 which adjusts the x—x axis of the log to the sawing plane of the saw to ensure that the first cut provides for a preselected minimum width board as shown by the dimension Z of the opening face 46 in FIGS. 15 and 16. The opening face 46 is parallel to the direction of cut of the saw 48, i.e. is parallel to the direction of feed as indicated by the arrow 50 in FIG. 16. This skew decision is then fed to the skew control as depicted at 52 in FIG. 1.

The skew control is then exercised for example by adjusting the relative positions of pushers or abutments 66 and i.e. minimum cut width face with the direction of travel of the log 10 to the saw 48.

This skew decision and rotational decision together with the information of the image analysis is fed to a further computer section 74 which determines the sawing solution. The equipment may automatically control the saw lines by both lateral adjustment of the log relative to the saw (as indicated by arrow 76 in FIG. 15) and rotation of the log (as indicated by arrow 78). Selected lateral and rotation adjustments are made at the appropriate times to cut the log in to boards having faces parallel to the face 46 (perpendicular to the line 64) or vice versa, i.e. perpendicular to the face 46 and parallel to the line 64.

The description has referred to locating knots as the material of high density, other imperfections or inclusions such as metal, rocks and rot can be located and taken into consideration in the sawing decision.

The above description has dealt with logs as this is the intent of the equipment but could be used to detect and locate areas of different densities in other bodies.

Having described the invention modifications will be evident to those skilled in the art without departing from the spirit of the invention as defined in the appended claims.

We claim:

1. A system for analyzing a body to determine the position of elements of different density than the body within said body comprising means to relatively move said body and a density scanner means in a direction along a path of travel, said density scanner means including a plurality of sources of electromagnetic energy located adjacent to and circumferentially spaced around said path and each positioned to pass electromagnetic energy through said body in a direction transversing said path as said body and said scanner means are relatively moved on said path, a sensor means for each said source for sensing the amount of said electromagnetic energy passing through said body from its respective of said sources, each said sensor means comprising plurality of discrete detectors arranged in circumferential side by side relationship on the opposite side of said path from its respective said source and each said detector adapted to detect the amount of radiation it receives from its respective said source thereby to provide signals of discrete values indicating the degree of attenuation of electromagnetic energy between each said discrete detector and its respective said source, means to generate an axial density signal based on radiation each said sensor detects over a length of said body as said body and said density scanner means are relatively moved, means for generating a longitudinal density plan from said axial density signals for each said sensor means, means for identifying areas representing said elements of different density in said body in each said density plan including means for separating components of said signal depicting said areas from signal components relating to geometry of said body.

2. A system as defined in claim 1 further comprising means for identifying areas representing the same one of said elements in each of said longitudinal density plans.

3. A system as defined in claim 2 further comprising means for reconstructing spaced discrete cross sections through said body representing a preselected length of said body with said elements in each said preselected length positioned in its respective of said reconstructed spaced discrete cross sections.

4. A system as defined in claim 3 wherein said body is a portion of log and said elements comprise knots in said portion.

5. A system as defined in claim 4 further comprising determining a longitudinal axis for said length of said log projecting said discrete cross sections parallel to said axis to provide an accumulated cross sectional density map of said selected length of said log identifying the propensity of knots in various angular positions around said axis.

6. A system as defined in claim 5 wherein a bounding polygon is determined for knots in said discrete cross section delineating the extremities of each of said knots.

7. A system as defined in claim 6 wherein each of said discrete cross-sections are each binary coded giving said bounding polygons one value and areas outside of said bounding polygons a second value.

8. A system as defined in claim 7 wherein each bounding polygon in each of said discrete cross sections is given a gray scale intensity value based on said preselected length so that the accumulated value of gray scale intensity in said accumulated cross sectional image is representative of the knots in that particular position along the length of said log.

9. A system as defined in claim 8 further comprising means for identifying a knot core in said accumulated cross sectional density map by selecting a threshold value of grey scale intensity representative of a preselected accumulation of knots and means for determining a bounding polygon bounding an area having a grey scale intensity above said threshold value from an area having a grey scale intensity below said threshold value.

10. A system defined in claim 7 further comprising means for determining a rotating decision for rotating said log about said selected axis based on the location and propensity of knots in said accumulated cross sectional density map.

11. A system as defined in claim 10 further comprising profiler means to determine the outer shape of the log as said log transverses and profiler means, means for providing a skewing decision for the said log based on said rotating decision and said outer shape of said log and skewing means for skewing said log relative to saw plane in accordance with said skewing decision.

12. A system as defined in claim 7 wherein at least three said circumferentially spaced sources each with a corresponding said sensor are provided whereby said means for generating generates at least three said longitudinal density plans.

13. A system as defined in claim 6 wherein each bounding polygon in each of said discrete cross sections is given a gray scale intensity value based on said preselected length so that the accumulated value of gray scale intensity in said accumulated cross sectional image is representative of the knots in that particular position along said length of said log.

14. A system as defined in claim 13 further comprising means for identifying a knot core in said accumulated cross sectional density map by selecting a threshold value of grey scale intensity representative of a preselected accumulation of knots and means for determining a bounding polygon bounding an area having a grey scale intensity above said threshold value from an area having a grey scale intensity below said threshold value.

15. A system as defined in claim 5 wherein each knot represented in each of said discrete cross sections is given a grey scale intensity value based on said preselected length so that the accumulated value of grey scale intensity in said accumulated cross sectional density map is representative of the number of knots in that particular angular position along said length of said log.

16. A system as defined in claim 15 wherein said means for identifying the same one of said elements in each of said plans includes means for determining axial end points of said elements in each of said longitudinal density plans, means for determining the approximate size of said elements in each of said plan views and means for selecting as the same element in each of said plans those elements having substantially the same size and having their axial end points located in said plan views in the same pair of axially spaced planes, said axially spaced planes being substantially perpendicular to the longitudinal axis of said plans.

17. A system as defined in claim 15 further comprising means for identifying a knot core in said accumulated cross sectional density map by selecting a threshold value of grey scale intensity representative of a preselected accumulation of knots and means for determining a bounding polygon bounding an area having a grey scale intensity above said threshold value from an area having a grey scale intensity below said threshold value.

18. A system defined in claim 6 further comprising means for determining a rotating decision for rotating said log about said selected axis based on the location and propensity of knots in said accumulated cross sectional density map.

19. A system as defined in claim 18 further comprising profiler means to determine the outer shape of the log as said log transverses and profiler means, means for providing a skewing decision for the said log based on said rotating decision and said outer shape of said log and skewing means for skewing said log relative to saw plane in accordance with said skewing decision.

20. A system as defined in claim 19 further comprising means for identifying the line of maximum height of said log as it transverses said profiler, means of applying an identifying line to said line of maximum height defined by the maximum spacing of said log from said conveyor, said line providing a datum for angular rotation of said log.

21. A system as defined in claim 5 wherein at least three said circumferentially spaced sources each with a corresponding said sensor are provided.

22. A system as defined in claim 5 wherein said means for identifying the same one of said elements in each of said plans includes means for determining axial end points of said elements in each of said longitudinal density plans, means for determining the approximate size of said elements in each of said plan views and means for selecting as the same element in each of said plan views those elements having substantially the same size and having their axial end points located in said plans in the same pair of axially spaced planes, said axially spaced planes being substantially perpendicular to the longitudinal axis of said plans.

23. A system as defined in claim 4 wherein a bounding polygon is determined for knots in said discrete cross section delineating the extremities of each of said knots.

24. A system as defined in claim 23 wherein each of said discrete cross-sections are each binary coded giving said bounding polygons one value and areas outside of said bounding polygons a second value.

25. A system as defined in claim 4 wherein at least three said circumferentially spaced sources each with a corresponding said sensor are provided.

26. A system as defined in claim 2 wherein said means for identifying the same one of said elements in each of said plans includes means for determining axial end points of said elements in each of said longitudinal density plans, means for determining the approximate size of said elements in each of said plan views and means for selecting as the same element in each of said plans those elements having substantially the same size and having their axial end points located in said plan views in the same pair of axially spaced planes, said axially spaced planes being substantially perpendicular to the longitudinal axis of said plans.

27. A method of reconstruction a cross section through a body illustrating the location of elements of a different density from the body in the body comprising projecting electromagnetic energy from at least two sources through said body as it moves on a path relative to said sources, said sources being circumferentially spaced around said path, detecting the amount of such electromagnetic energy transversing said body issuing from each said source using a sensor composed of a plurality of detectors arranged in side by side circumferential relationship on the opposite side of said path from its respective of said sources to determine local densities of said body based on the amount of electromagnetic energy received by each detector and generating a projected longitudinal plan view of said local densities of said body for each said sensor, each said plan views having ares of different grey scale intensities dependent on the amount of electromagnetic energy received by said detector and representative of elements of different densities in said body, analyzing said plan views to find areas representing substantially the same size element and having end points in the same pair of spaced parallel planes substantially perpendicular to the longitudinal axis of said plan views and spaced longitudinally along said longitudinal axis thereby to define areas representing the same element in each of said plan views.

28. A method as defined in claim 27 further comprising reconstructing cross sections of said body at least at some axial positions along said longitudinal axis corresponding with at least some of said elements and positioning said at least some of said elements within said reconstructed cross sections.

29. A method as defined in claim 28 wherein said body is a log and said elements are knots within said log.

30. A method as defined in claim 29 further comprising reconstructing a cross section for a plurality of said knots along the length of said log.

31. A method as defined in claim 30 further comprising binary coded representations of said log in each of said cross sections with a grey scale intensity value selected in accordance with the relative axial length of said knot to the axial length of said log.

32. A method as defined in claim 31 further comprising defining a longitudinal axis for said log and axially projecting each of said cross sections parallel to said longitudinal axis to provide an accumulated axially projected cross sectional map of said log, said cross sectional map representing areas of different knot propensities with different grey scale intensities depending on the accumulation of grey scale intensities representing the number of knots located along a projected local area of said axial projection.

33. A method as defined in claim 32 further comprising analyzing said grey scale intensity of said accumulated cross sectional map to determine a knot core based on a selected grey scale intensity for said knot core.

34. A method of analyzing a log to provide a rotational decision for sawing comprising determining a plurality of spaced cross sections of said log having knots positioned therein, defining a longitudinal axis of said log, applying a grey scale intensity to each knot located in each of said cross sections, projecting said grey scale intensity for said knots parallel to said longitudinal axis of said log to form a grey scale cross sectional image varying in grey scale intensity in various areas depending on the number of knot representations projected into said various areas of said image.

35. A method as defined in claim 34 further comprising determining a knot core in said cross section by selecting a threshold grey scale intensity for said knot core and determining a bounding polygon based on said thresholding value.

36. A method as defined in claim 35 further comprising determining a maximum diagonal length for said knot core and providing a rotation decision based on the angular position of said maximum diagonal.

* * * * *